United States Patent
Bohm

(10) Patent No.: US 7,059,352 B2
(45) Date of Patent: Jun. 13, 2006

(54) TRIGGERABLE PASSIVE VALVE FOR USE IN CONTROLLING THE FLOW OF FLUID

(75) Inventor: Sebastian Bohm, Los Gatos, CA (US)

(73) Assignee: LifeScan Scotland, Inverness (GB)

( * ) Notice: Subject to any disclaimer, the term of this patent is extended or adjusted under 35 U.S.C. 154(b) by 0 days.

(21) Appl. No.: 11/096,036

(22) Filed: Mar. 30, 2005

(65) Prior Publication Data

US 2005/0217743 A1    Oct. 6, 2005

Related U.S. Application Data

(60) Provisional application No. 60/558,390, filed on Mar. 31, 2004, provisional application No. 60/558,375, filed on Mar. 31, 2004.

(51) Int. Cl.
*F15C 1/04* (2006.01)

(52) U.S. Cl. ............... 137/828; 137/833; 204/601; 204/605; 422/100

(58) Field of Classification Search ............. 137/828, 137/833; 204/601, 604, 605; 422/100
See application file for complete search history.

(56) References Cited

U.S. PATENT DOCUMENTS

| | | | |
|---|---|---|---|
| 4,676,274 A | 6/1987 | Brown | |
| 5,922,591 A | 7/1999 | Anderson et al. | |
| 5,969,736 A * | 10/1999 | Field et al. | 347/85 |
| 6,130,098 A | 10/2000 | Handique et al. | |
| 6,143,248 A | 11/2000 | Kellogg et al. | |
| 6,153,073 A * | 11/2000 | Dubrow et al. | 204/453 |
| 6,261,431 B1 * | 7/2001 | Mathies et al. | 204/601 |
| 6,326,211 B1 | 12/2001 | Anderson et al. | |
| 6,866,822 B1 | 3/2005 | House et al. | |
| 2002/0114738 A1 | 8/2002 | Wyzgol et al. | |
| 2002/0141903 A1 | 10/2002 | Parunak et al. | |
| 2002/0143437 A1 | 10/2002 | Handique et al. | |
| 2003/0070677 A1 | 4/2003 | Handique et al. | |
| 2004/0096959 A1 | 5/2004 | Stiene et al. | |
| 2004/0099321 A1 * | 5/2004 | Schoeniger et al. | 137/828 |
| 2004/0109790 A1 | 6/2004 | Shartle et al. | |

FOREIGN PATENT DOCUMENTS

| | | |
|---|---|---|
| WO | WO 97/21090 | 6/1997 |
| WO | WO 00/22436 | 4/2000 |
| WO | WO 01/88525 | 11/2001 |

(Continued)

OTHER PUBLICATIONS

U.S. Appl. No. 10/811,446, filed Mar. 26, 2004.

(Continued)

*Primary Examiner*—A. Michael Chambers
(74) *Attorney, Agent, or Firm*—Bernard Shay

(57) ABSTRACT

The present invention is directed to valves for use in controlling the flow of fluid and, more particularly, to a triggerable passive valve for use in controlling the flow of fluid. In one embodiment, a fluid delivery channel is connected to a flow restrictor and a passive valve positioned in the fluid delivery channel downstream from the flow restrictor. The first passive valve prevents fluid from moving through the channel when the pressure exerted by the fluid on the first passive valve is below the burst pressure. A pneumatic actuator actuates the valve by forcing fluid through the passive valve.

5 Claims, 6 Drawing Sheets

FOREIGN PATENT DOCUMENTS

| WO | WO 02/07884 | 1/2002 |
|---|---|---|
| WO | WO 02/41995 | 5/2002 |
| WO | WO 02/42650 | 5/2002 |
| WO | WO 02/78845 | 10/2002 |
| WO | WO 03/012406 | 2/2003 |

OTHER PUBLICATIONS

U.S. Appl. No. 10/883,585, filed Jun. 30, 2004.

Jun Zeng, et al., "Fluidic Capacitance Model of Capillary Driven Stop Valves" ASME 2000, Microcosm Technologies, Inc., Cambridge, MA 02142, pp. 1-7.

Richard M. Moroney, et al., "A Passive Fluid Valve Element for a High-density Chemical Synthesis Machine", Sarnoff Corporation CN-5300, Princeton, NJ 08543, pp. 1-4.

P.F. Man, et al., "Microfabricated Capillary-Driven Stop Valve and Sample Injector" MEMS 98, Jan. 25-29, 1998, Heidelberg, Germany, pp. 45-50, 1998 IEEE.

Brett R. Wenner, et al., "Biosensing on the CD Microfluidic Platform with Genetically Engineered Proteins", 2000 Society of Automotive Engineers, Inc., pp. 1-6, 2000-01-2513.

Marc J. Madou, et al., "Design and Fabrication of CD-like Microfluidic Platforms for Diagnostics: Microfluidic Functions", Biomedical Microdevices 3:3, 245-254, 2001 Kluwer Academic Publishers, Manufactured in the Netherlands.

K. Handique, et al., "On-Chip Thermopneumatic Pressure for Discrete Drop Pumping", Analytical Chemistry, vol. 73, No. 8, Apr. 15, 2001, The University of Michigan, Ann Arbor, Michigan 48109-2136, pp. 1831-1838.

K. Handique, et al., "Nanoliter Liquid Metering in Microchannels Using Hydrophobic Patterns", Analytical Chemical Society Pub. On Web Aug. 3, 2000, The University of Michigan, Ann Arbor, Michigan 48109-2136, pp. 4100-4109, No. 72.

* cited by examiner

TRIGGERABLE PASSIVE VALVE FOR USE IN CONTROLLING THE FLOW OF FLUID

CROSS-REFERENCE

This application claims the benefit of U.S. Provisional Application No. 60/558,390, filed Mar. 31, 2004, which application is incorporated herein by reference. This application claims the benefit of U.S. Provisional Application No. 60/558,375, filed Mar. 31, 2004, which application is incorporated herein by reference.

This application is related to the following copending patent applications: application Ser. No. 11/096,005; and application Ser. No. 11/096,035; and application Ser. No. 11/095,374; and application Ser. No. 11/095,635; and application Ser. No. 11/095,636; which are hereby incorporated herein by reference.

BACKGROUND OF THE INVENTION

The present invention relates, in general, to valves for use in controlling the flow of fluid and, more particularly, to a triggerable passive valve for use in controlling the flow of fluid.

SUMMARY OF THE INVENTION

The present invention is directed to a triggerable passive valve for use in controlling the flow of fluid. A triggerable passive valve according to one embodiment of the present invention includes: A fluid delivery channel having an inlet for receiving fluid and an outlet for discharging fluid, the outlet being downstream from the inlet. A flow restrictor positioned between the inlet and the outlet, a first passive valve positioned in the fluid delivery channel downstream from the flow restrictor. The first passive valve having a first predetermined burst pressure, the first passive valve preventing fluid from moving through the channel when the pressure exerted by the fluid on the first passive valve is below the burst pressure. A control channel that includes an inlet and an outlet. The control channel outlet being connected to the fluid delivery channel between the flow restrictor and the first passive valve. A pneumatic actuator connected to the control channel at the control channel inlet. And, a second passive valve positioned in the control channel between the control channel inlet and the control channel outlet.

A triggerable passive valve according to a further embodiment of the present invention includes: A fluid delivery channel having an inlet for receiving fluid and an outlet for discharging fluid downstream from the inlet. A flow restrictor positioned between the inlet and the outlet, the flow restrictor including a length of the delivery channel having a cross sectional area which is smaller than a cross sectional area of the channel at the inlet. A first passive valve positioned in the fluid delivery channel downstream from the flow restrictor, the first passive valve having a first predetermined burst pressure, the first passive valve preventing fluid from moving through the channel when the pressure exerted by the fluid on the first passive valve is below the burst pressure, the first passive valve including a hydrophobic patch positioned on one wall of the fluid delivery channel, the hydrophobic patch including a material having a contact angle of between seventy and one hundred eighty degrees. A control channel having an inlet and an outlet, the control channel outlet being connected to the fluid delivery channel between the flow restrictor and the first passive valve. A pneumatic actuator connected to the control channel at the control channel inlet, the pneumatic actuator including an air chamber, an electrical heater adapted to heat air in the air chamber and a controller connected to the electrical heater. A vent, positioned to release air from the pneumatic actuator when pressure in the pneumatic actuator exceeds a predetermined limit. A second passive valve positioned in the control channel between the control channel inlet and the control channel outlet, the second passive valve including:
a hydrophobic patch positioned on one wall of the fluid delivery channel, the hydrophobic patch including a material having a contact angle of between seventy and one hundred eighty degrees.

A triggerable passive valve according to a further embodiment of the present invention includes: A fluid delivery channel having an inlet for receiving fluid and an outlet for discharging fluid downstream from the inlet. A flow restrictor positioned between the inlet and the outlet. A first passive valve positioned in the fluid delivery channel downstream from the flow restrictor, the first passive valve having a first predetermined burst pressure, the first passive valve preventing fluid from moving through the channel when the pressure exerted by the fluid on the first passive valve is below the burst pressure. A bubble chamber connected to the fluid delivery channel between the flow restrictor and the first passive valve. A second passive valve positioned in the control channel between the control channel inlet and the control channel outlet.

A triggerable passive valve according to a further embodiment of the present invention includes: A fluid delivery channel having an inlet for receiving fluid and an outlet for discharging fluid downstream from the inlet. A flow restrictor positioned between the inlet and the outlet, the flow restrictor including a length of the delivery channel having a cross sectional area which is smaller than a cross sectional area of the channel at the inlet. A first passive valve positioned in the fluid delivery channel downstream from the flow restrictor, the first passive valve having a first predetermined burst pressure, the first passive valve preventing fluid from moving through the channel when the pressure exerted by the fluid on the first passive valve is below the burst pressure, the first passive valve including a hydrophobic patch positioned on one wall of the fluid delivery channel, the hydrophobic patch including a material having a contact angle of between seventy and one hundred eighty degrees. A control channel having an inlet and an outlet, the control channel outlet being connected to the fluid delivery channel between the flow restrictor and the first passive valve. A bubble chamber connected to the fluid delivery channel between the flow restrictor and the first passive valve, the bubble chamber including an electrical heater adapted to heat fluid in the fluid delivery channel, wherein the electrical heater includes a resistor and a controller connected to the electrical heater. A second passive valve positioned in the control channel between the control channel inlet and the control channel outlet, the second passive valve including a hydrophobic patch positioned on one wall of the fluid delivery channel, the hydrophobic patch including a material having a contact angle of between seventy and one hundred eighty degrees.

A triggerable passive valve according to a further embodiment of the present invention includes: A fluid delivery channel having an inlet for receiving fluid and an outlet for discharging fluid downstream from the inlet. A flow restrictor positioned between the inlet and the outlet, the flow restrictor including a length of the delivery channel having a cross sectional area which is smaller than a cross sectional area of the channel at the inlet. A first passive valve positioned in the fluid delivery channel downstream from the flow restrictor, the first passive valve having a first predetermined burst pressure, the first passive valve preventing fluid from moving through the channel when the pressure exerted by the fluid on the first passive valve is below the burst pressure, the first passive valve including a hydrophobic patch positioned on one wall of the fluid delivery channel, the hydrophobic patch including a material having a contact angle of between seventy and one hundred eighty degrees. A control channel having an inlet and an outlet, the control channel outlet being connected to the fluid delivery channel between the flow restrictor and the first passive valve. A bubble chamber connected to the fluid delivery channel between the flow restrictor and the first passive valve, the bubble chamber including an electrical heater adapted to heat fluid in the fluid delivery channel, wherein the electrical heater includes a pair of opposed electrodes. A controller connected to the electrical heater. A second passive valve positioned in the control channel between the control channel inlet and the control channel outlet, the second passive valve including a hydrophobic patch positioned on one wall of the fluid delivery channel, the hydrophobic patch including a material having a contact angle of between seventy and one hundred eighty degrees.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figures 1, 2:
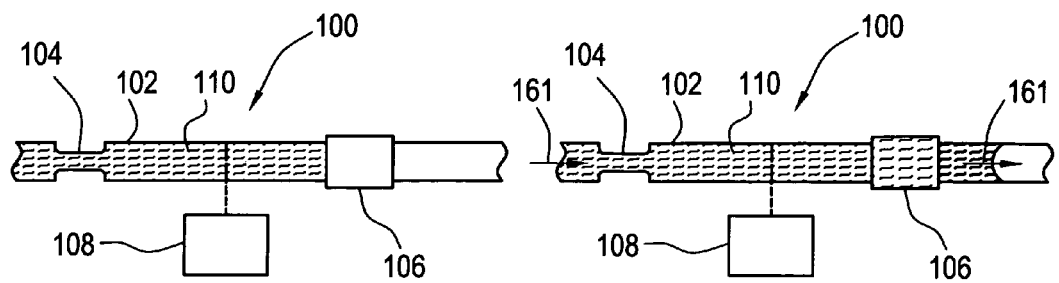
FIG. 1 is an illustration of a triggerable passive valve according to an embodiment of the present invention. The triggerable passive valve embodiment illustrated in FIG. 1 includes a flow restrictor, a pressurizing device, and a first passive valve, connected with a fluid delivery channel. The triggerable passive valve embodiment illustrated in FIG. 1 acts upon a sample liquid.
FIG. 2 is an illustration of the triggerable passive valve of FIG. 1 after its pressurizing device has increased pressure on the sample liquid, causing sample liquid to flow beyond the passive valve.

The triggerable passive valves 100 illustrated in FIGS. 1 through 14 can be used in microfluidic circuits 160 as illustrated in FIGS. 15 through 18. Microfludic circuits 160 include analyte sensors 162 that can be used to measure analyte in sample liquid 110. Sample liquid 110 can be a variety of biological fluids, including interstitial fluid, whole blood, or plasma.

When the pressurizing device 108 illustrated in FIGS. 1 through 18 is not activated, the driving force for flow through fluid delivery channel 102 can include capillary, gravitational, and centrifugal forces. It can also include force provided by way of pressurized gas, or a pump. In addition, the driving force for flow can include force applied to the sample at its source. For example, force can be provided by pressure in dermal tissue when the sample is interstitial fluid.

In the triggerable passive valves 100 and microfluidic circuits 160 illustrated in FIGS. 1 through 18, channels can be rectangular, square, or semicircular in cross section. When rectangular in cross section, channels may be easier to manufacture. The length, width, and depth of the channels vary, but are generally on the order of 25 to 2500 microns, and are often 500 microns or less. Triggerable passive valves 100 and microfluidic circuits 160 can be constructed by way of laminated layers of plastic bonded with adhesive, or can be injection molded plastic. Suitable plastics include polyester, polycarbonate, acrylic, polystyrene, polyolefins, polyimides, and any other thermoplastic polymer. Triggerable passive valves 100 may also be constructed using etched silicon or glass.

FIG. 1 is an illustration of a triggerable passive valve 100 according to an embodiment of the present invention. Triggerable passive valve 100 includes a flow restrictor 104, a pressurizing device 108, and a first passive valve 106, connected with fluid delivery channel 102. Triggerable passive valve 100 acts upon sample liquid 110. As sample liquid 110 flows into fluid delivery channel 102, it stops at first passive valve 106. For flow to occur beyond first passive valve 106, the pressure of sample liquid 110 must exceed the burst pressure of first passive valve 106. The burst pressure of first passive valve 106 is determined by its geometry and physical properties, as will be explained later. When activated, Pressurizing device 108 exerts pressure on sample liquid 110, increasing its pressure to a value higher than the burst pressure of first passive valve 106, causing sample liquid 110 to move past first passive valve 106. Most of the sample liquid 110 flows in the direction of first passive valve 106, rather than in the direction of flow restrictor 104. This is because flow restrictor 104 has a higher resistance to flow once first passive valve 106 has been breached. Once flow beyond first passive valve 106 occurs, the pressure exerted upon sample liquid 110 by pressurizing device 108 can be removed.

FIG. 2 is an illustration of triggerable passive valve 100 of FIG. 1 after pressurizing device 108 has increased pressure on sample liquid 110, causing sample liquid 110 to flow beyond passive valve 106. After flowing beyond first passive valve 106, sample liquid 110 continues to flow along fluid delivery channel 102 as indicated by arrows 161.

Figures 3, 4:
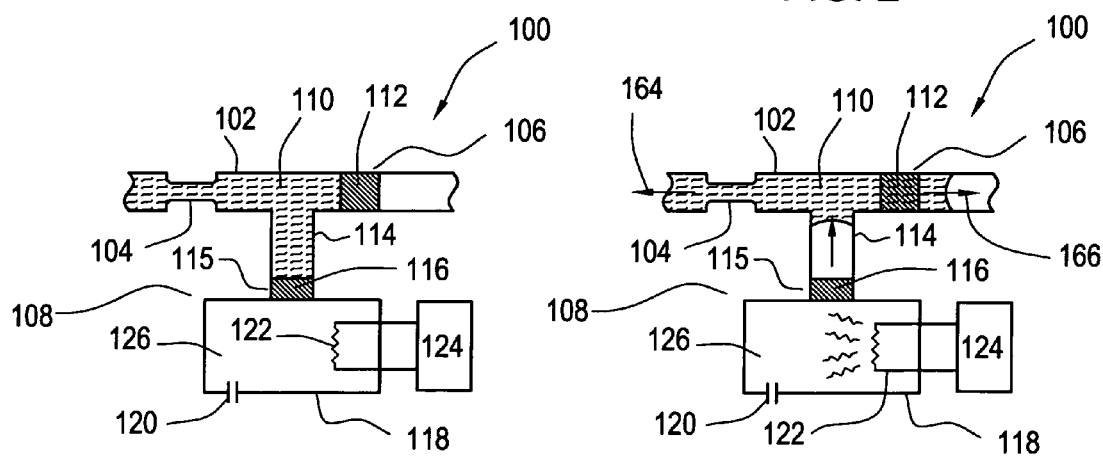
FIG. 3 is an illustration of another triggerable passive valve according to an embodiment of the present invention. The triggerable passive valve embodiment illustrated in FIG. 3 includes a flow restrictor, a pressurizing device, and a first passive valve, connected with a fluid delivery channel. The triggerable passive valve embodiment illustrated in FIG. 3 acts upon a sample liquid, and includes a heater in the pressurizing device for increasing the temperature and pressure of air in the pressurizing device.
FIG. 4 is an illustration of the triggerable passive valve of FIG. 3 after the heater has increased the temperature and pressure of air in the pressurizing device, causing sample liquid to flow beyond the passive valve.

FIG. 3 is an illustration of another triggerable passive valve 100 according to an embodiment of the present invention. Triggerable passive valve 100 includes a flow restrictor 104, a pressurizing device 108, and a first passive valve 106, connected by fluid delivery channel 102. Triggerable passive valve 100 acts upon sample liquid 110, and includes electrical heater 122 in pressurizing device 108 for increasing the temperature and pressure of air 126 in air chamber 118. Pressurizing device 108 also includes control channel 114, second passive valve 115, vent 120 and controller 124. Vent 120 would allow air to pass but would be impermeable to fluid to prevent fluid from leaking out of vent 120. First passive valve 106 includes hydrophobic patch 112, while second passive valve 115 includes hydrophobic patch 116. First passive valve 106 has a first burst pressure, and second passive valve 115 has a second burst pressure. The first and second burst pressures can be the same, or different. Between flow restrictor 104 and first passive valve 106 is control channel 114. Control channel 114 is connected to fluid delivery channel 102 on one end, and to second passive valve 115 on the other. Second passive valve 115 is connected to air chamber 118. Vent 120 allows pressure in air chamber 118 to remain at atmospheric while sample liquid 110 flows through control channel 114 and to the edge of second passive valve 115. Second passive valve 115 prevents sample liquid 110 from entering air chamber 118. Electrical heater 122 can be used to increase temperature and pressure in air chamber 118. Electrical heater 122 is controlled by controller 124. As illustrated in FIG. 3, sample liquid 110 has entered fluid delivery channel 102 by way of flow restrictor 104 and has stopped at both first passive valve 106 and second passive valve 115. Once sample liquid 110 has entered fluid delivery channel 102 and reached first passive valve 106 and second passive valve 115, electrical heater 122 is turned on.

FIG. 4 is an illustration of the triggerable passive valve 100 of FIG. 3 after electrical heater 122 has been turned on and has increased the temperature and pressure of air 126 in air chamber 118. When electrical heater 122 is on, vent 120 may be opened or closed, depending upon its design. Electrical heater 122 heats air 126 in air chamber 118, increasing its temperature and pressure. As the pressure in air chamber 118 increases, the pressure of sample liquid 110 increases. When the pressure of sample liquid 110 exceeds the first burst pressure, it flows out of control channel 114 and beyond first passive valve 106 and flow restrictor 104. Arrows 164 and 166 indicate the direction of flow. Once first passive valve 106 is breached, there is less resistance to flow in the direction of arrow 166 than in the direction of arrow 164. This is due to the geometry of flow restrictor 104. Flow restrictor 104 has a higher resistance to flow than fluid delivery channel 102 in the vicinity of first passive valve 106 because the cross sectional area of flow restrictor 104 is less than that of fluid delivery channel 102. Because of the lower resistance to flow encountered at flow restrictor 104, most of the sample displaced from control channel 114 flows in the direction indicated by arrow 166. Once flow across first passive valve 106 has been established, electrical heater 122 is turned off, as illustrated in FIG. 5.

Figure 5:
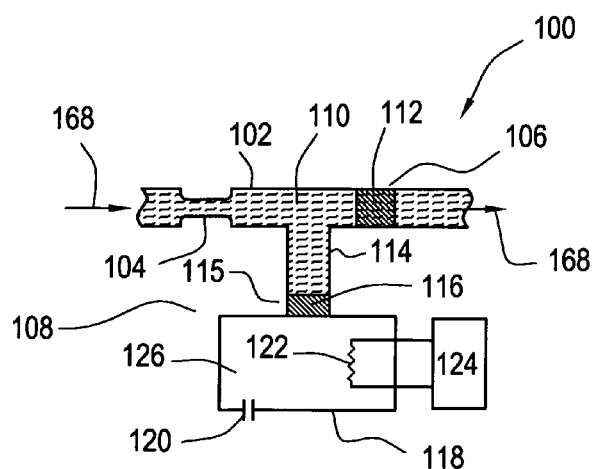
FIG. 5 is an illustration of the triggerable passive valve of FIG. 4 after the heater has been turned off and the air in the pressurizing device has returned to its original temperature and pressure.

FIG. 5 is an illustration of the triggerable passive valve 100 of FIG. 4 after electrical heater 122 has been turned off and air 126 in air chamber 118 has returned to atmospheric pressure. When electrical heater 122 is turned off, vent 120 is opened (if it is not already open), and air 126 in air chamber 118 returns to atmospheric pressure. This causes sample liquid 110 in control channel 114 to flow back to second passive valve 115. Sample liquid 110 stops at second passive valve 115 because the pressure in sample liquid 110 is less than the second burst pressure. Since flow over first passive valve 106 has been established, sample liquid 110 continues to flow through fluid delivery channel 102 as indicated by arrows 168.

In reference to the triggerable passive valve 100 illustrated in FIGS. 3 through 5, first passive valve 106 includes hydrophobic patch 112 while second passive valve 115 includes hydrophobic patch 116. Hydrophobic patches 112 and 116 allow air to pass, but resist the flow of sample liquid 110. This is because they repel aqueous samples, such as interstitial fluid, blood, and plasma. For flow of aqueous sample to occur beyond patches 112 and 116, the pressure of sample liquid 110 must exceed the burst pressure of hydrophobic patches 112 and 116. The burst pressure is determined by the channel geometry, the physical properties of its surfaces, and the physical properties of the sample liquid 110. In designing triggerable passive valve 100, burst pressures can be selected that allow flow of sample liquid 110 beyond first passive valve 106 and hydrophobic patch 112 after increasing the pressure of sample liquid 110. Hydrophobic patches 112 and 116 can be fabricated using commercially available hydrophobic inks, and various printing techniques including screen printing, gravure, slot coating, flexo, offset, and spray coating. For example, the ink FluoroPel PFC MH can be used to form hydrophobic patches 112 and 116. FluoroPel PFC MH can be purchased from Cytonix Inc., of Beltsville, Md. When screen printed onto polyester, FluoroPel PFC MH forms a hydrophobic area having a contact angle with water of approximately 150 degrees. When characterizing the wettability of a surface, its contact angle with water is often measured. To do this, a drop of water is placed onto the surface, and the angle is measured between the surface and a line drawn tangent to the liquid drop. As a point of reference, completely hydrophobic material has a contact angle with water of 180 degrees, while untreated polyester has a contact angle of approximately 70 degrees. Hydrophilic surfaces can have a contact angle as low as 0 degrees. In this invention, hydrophobic patches 112 and 116 typically have a contact angle between 70 and 180 degrees, whereas hydrophilic surfaces typically have a contact angle between 0 and 70 degrees. Cytonix offers hydrophobic ink formulations that have been optimized for use with other types of printing, such as flexo and offset, as well as spray coating. Hydrophobic inks such as those used in printing microscope slides are also suitable for use in printing hydrophobic areas. Alternatively, commercially available screen printing inks can be modified for use in printing hydrophobic areas. For example, Zonyl fluoroadditives, sold by DuPont Corporation of Delaware, can be used as an additive to traditional screen printing inks.

A structural passive valve useable in place of hydrophobic areas 112 or 116 may also be formed by a sudden widening in the channel (e.g. a widening in channel 102 if used to replace hydrophobic area 112 or a widening in channel 114 if used to replace hydrophobic area 116) such that when a liquid front reaches the sudden widening, a meniscus is formed at the point of the widening (angle preferable more acute than 90 degrees. In order for the liquid to move into the wider section of the channel, the liquid needs to be pressurized so that the menicus is pushed 'around the edge' thereby wetting the wider area. This requires, as with the hydrophobic based passive valve, a minimum pressure which is referred to as burst pressure.

The performance of pressurizing devices 108, as illustrated in FIGS. 3 through 5, depend upon the volume of air chamber 118, the size of vent 120, and the heat provided by electrical heater 122. A small air chamber volume, combined with a high heating rate and small vent, result in rapid build up of pressure in air chamber 118. During design, the air chamber volume, the heating rate, and the vent size are carefully selected to provide sufficient pressure while minimizing power requirements. In some designs, vent 120 is opened and closed using a mechanical device, such as a plunger. In other designs, it a vent 120 is used that is always open to atmosphere. Using a vent that is always open to atmosphere may simplify mechanical requirements for the system. Referring again to FIGS. 3 through 5, when a vent 120 is always open to atmosphere, sample liquid 110 flows through fluid delivery channel 102 and control channel 114 and up to the edge of first passive valve 106 and second passive valve 115, while the air 126 in chamber 118 remains at atmospheric pressure. When electrical heater 122 is turned on, pressure builds in air chamber 118 faster than it vents through vent 120. Buildup of pressure in air chamber 118 causes an increase in the pressure of sample liquid 110, breaching first passive valve 106, and displacing sample liquid 110 from control channel 114. When electrical heater 122 is turned off, air chamber 118 cools, returning air chamber 118 to atmospheric pressure. Sample liquid 110 flows into control channel 114 as air chamber 118 returns to atmospheric pressure. Vent 120 can be formed by making a hole in the material that covers air chamber 118, or it can be formed using a channel between air chamber 118 and the atmosphere. Channels can be fabricated using laminates or injection molding, or with techniques outlined earlier. Electrical heater 120 can be part of triggerable passive valve 100, or can be external. In the case where it is part of a triggerable passive valve 100, it can be a printed electrical resistor.

Figure 6:
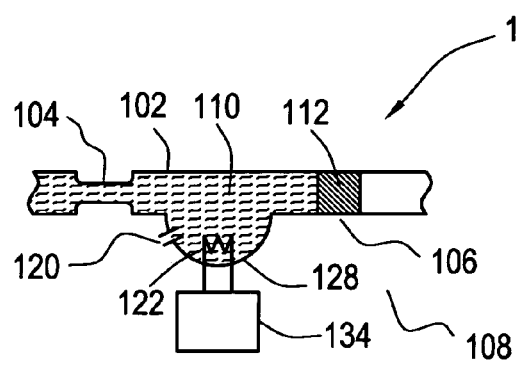
FIG. 6 is an illustration of another triggerable passive valve according to an embodiment of the present invention. The triggerable passive valve embodiment illustrated in FIG. 6 includes a flow restrictor, a pressurizing device, and a first passive valve, connected by a fluid delivery channel. The triggerable passive valve embodiment illustrated in FIG. 6 acts upon a sample liquid, and includes a heater in the pressurizing device for vaporizing a portion of the sample liquid.

FIG. 6 is an illustration of another triggerable passive valve 100 according to an embodiment of the present invention. Triggerable passive valve 100 includes a flow restrictor 104, a pressurizing device 108, and first passive valve 106, connected by fluid delivery channel 102. Triggerable passive valve 100 acts upon sample liquid 110, and includes electrical heater 122 in pressurizing device 108 for vaporizing a portion of sample liquid 110. Pressurizing device 108 also includes bubble chamber 128, vent 120, and controller 134. First passive valve 106 includes hydrophobic patch 112. Triggerable passive valve 100 acts upon sample liquid 110. Bubble chamber 128 is located between flow restrictor 104 and first passive valve 106, and fills completely as sample liquid 110 flows through flow restrictor 104 to the edge of first passive valve 106. Electrical heater 122 is controlled by controller 134.

Figure 7:
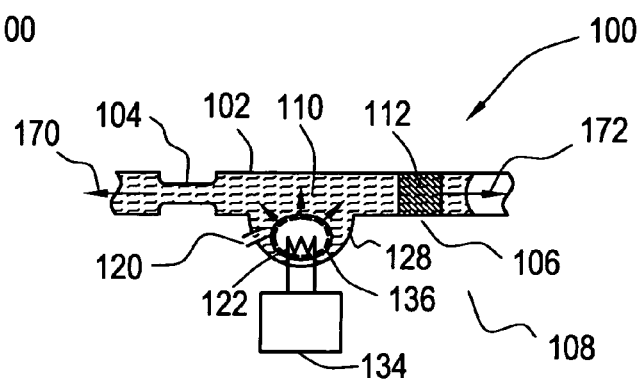
FIG. 7 is an illustration of the triggerable passive valve of FIG. 6 after the heater has vaporized a portion of the sample liquid, increasing pressure in the sample liquid and causing sample liquid to flow beyond the passive valve.
Figure 8:
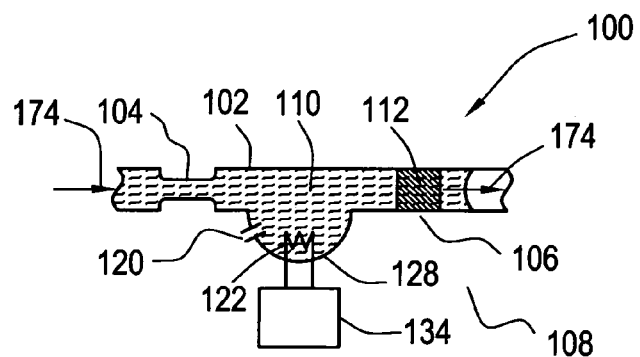
FIG. 8 is an illustration of the triggerable passive valve of FIG. 7 after the heater has been turned off, and the vaporized portion of sample liquid has been removed.

FIG. 7 is an illustration of the triggerable passive valve 100 of FIG. 6 after electrical heater 122 has vaporized a portion of the sample liquid 110, thereby increasing pressure in sample liquid 110 and causing sample liquid 110 to flow beyond passive valve 106. Electrical heater 122 vaporizes a portion of sample liquid 110 in bubble chamber 128, forming vapor bubble 136. As vapor bubble 136 expands, it displaces sample liquid 110 from bubble chamber 128, increasing the pressure of sample liquid 110, and causing flow towards first passive valve 106 and flow restrictor 104. Arrows 170 and 172 indicate the flow of sample liquid 110. As described earlier, most of sample liquid 110 flows is in the direction indicated by arrow 172, due to resistance in the direction of flow restrictor 104. Once first passive valve 106 has been breached, electrical heater 122 is turned off, and sample liquid 110 flows in the direction of arrow 172 only. Vapor bubble 136 remains in bubble chamber 128 as sample liquid 110 flows through fluid delivery channel 102, over first passive valve 106, and in the direction of arrow 172. In some instances, it may be desirable to remove vapor bubble 136 after first passive valve 106 has been breached, and for that reason vent 120 is provided. Vent 120 provides direct contact between atmosphere and vapor bubble 136, and can be always open, or opened after first passive valve 106 has been breached. FIG. 8 is an illustration of the triggerable passive valve 100 of FIG. 7 after electrical heater 122 has been turned off, and vapor bubble 136 has been removed by venting to atmosphere using vent 120. Referring to FIG. 8, first passive valve 106 has been breached, and sample liquid 110 continues to flow through fluid delivery channel 102 and over first passive valve 106, as indicated by arrows 174.

Another approach can be used to generate a bubble, as used in the triggerable passive valve 100 illustrated in FIGS. 6 through 8. Instead of using an electrical heater 122 to vaporize a small portion of sample liquid 110, a bubble can be generated using electrolysis. This can be done by replacing electrical heater 122 with a pair of electrodes, and forcing current between them. When sample liquid is simultaneously in contact with both electrodes and current is applied, Oxygen is formed on one electrode while Hydrogen is formed on the other. The Oxygen and Hydrogen combine to form a bubble that provides pressure to breach passive valve 106. A triggerable passive valve 100 that uses hydrolysis to form a bubble is illustrated in FIGS. 9 through 11.

Figure 9:
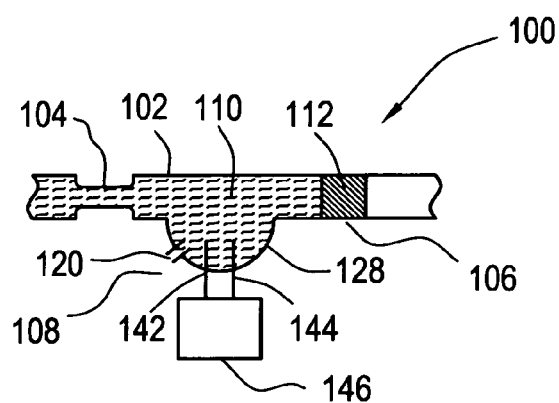
FIG. 9 is an illustration of another triggerable passive valve according to an embodiment of the present invention. The triggerable passive valve embodiment illustrated in FIG. 9 includes a flow restrictor, a pressurizing device, and a first passive valve, connected by a fluid delivery channel. The triggerable passive valve embodiment illustrated in FIG. 9 acts upon a sample liquid, and includes a pair of electrodes in the pressurizing device for electrolyzing a portion of the sample liquid.

FIG. 9 is an illustration of another triggerable passive valve 100 according to an embodiment of the present invention. Triggerable passive valve includes flow restrictor 104, pressurizing device 108, and first passive valve 106, connected by fluid delivery channel 102. Triggerable passive valve 100 acts upon sample liquid 110, and includes first electrode 142, and second electrode 144 for electrolyzing a portion of sample liquid 110. Pressurizing device 108 also includes bubble chamber 128 and controller 146. First passive valve 106 includes hydrophobic patch 112. Bubble chamber 128 is located between flow restrictor 104 and first passive valve 106, and fills completely as sample liquid 116 flows through flow restrictor 104 and to the edge of first passive valve 106. When bubble chamber 128 is filled with sample liquid 110, first electrode 142 and second electrode 144 are simultaneously in direct contact with sample liquid 110. First electrode 142 and second electrode 144 are controlled with controller 146.

Figure 10:
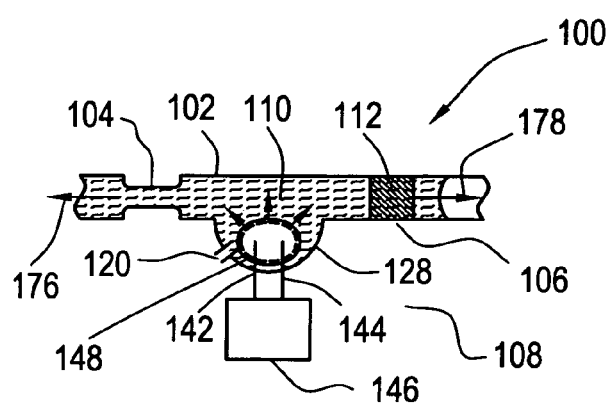
FIG. 10 is an illustration of the triggerable passive valve of FIG. 9 after current has been applied to the pair of electrodes, thus electrolyzing a portion of the sample liquid which increases the pressure of the sample liquid and causes sample liquid to flow beyond the passive valve.
Figure 11:
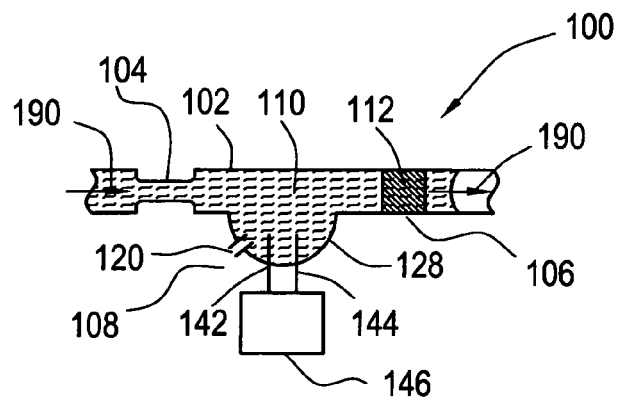
FIG. 11 is an illustration of the triggerable passive valve of FIG. 10 after current is removed from the pair of electrodes and the gasses produced by electrolysis have been removed.

FIG. 10 is an illustration of the triggerable passive valve 100 of FIG. 9 after current has been applied between first electrode 142 and second electrode 144. Applying current between first electrode 142 and second electrode 144 causes electrolysis in a portion of sample liquid 110, increasing the pressure of sample liquid 110 and causing sample liquid 110 to flow beyond passive valve 106. When current is applied between first electrode 142 and second electrode 144, Oxygen and Hydrogen form at first electrode 142 and second electrode 144. The Oxygen and Hydrogen combine forming electrolysis bubble 148. Electrolysis bubble 148 displaces sample liquid 110 from bubble chamber 128, increasing the pressure of sample liquid 110. This causes flow in the directions of first passive valve 106 and flow restrictor 104, as indicated by arrows 178 and 176. Most of the flow is in the direction indicated by arrow 178, due to resistance encountered at flow restrictor 104. Once first passive valve 106 has been breached, current between first electrode 142 and second electrode 144 is turned off, and sample liquid 110 flows in the direction of arrow 178 only. Electrolysis bubble 148 remains in bubble chamber 128 as sample liquid 110 flows through fluid delivery channel 102, over first passive valve 106, and in the direction of arrow 178. In some instances, it is desirable to remove electrolysis bubble 148 after first passive valve 106 has been breached. In that case, vent 120 is used. Vent 120 provides direct contact between atmosphere and electrolysis bubble 148, and can be always open, or opened after first passive valve 106 has been breached. FIG. 11 is an illustration of the triggerable passive valve 100 of FIG. 10 after current is turned off between first electrode 142 and second electrode 144, and electrolysis bubble 148 has been vented to atmosphere using vent 120. Since first passive valve 106 has been breached, sample liquid 110 continues to flow through fluid delivery channel 102 and over first passive valve 106, as indicated by arrows 190.

Figures 12, 13:
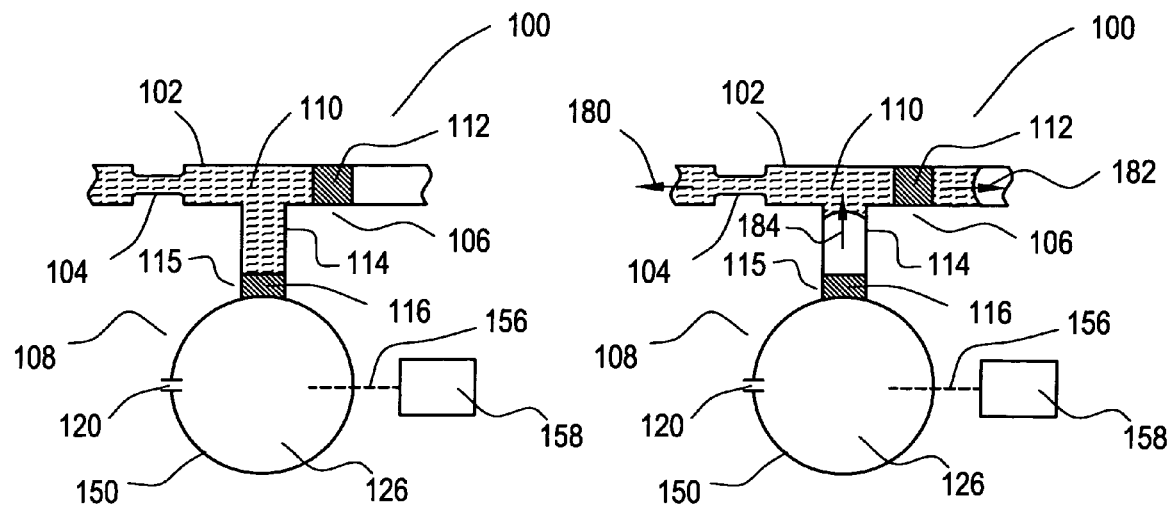
FIG. 12 is an illustration of another triggerable passive valve according to an embodiment of the present invention. The triggerable passive valve embodiment illustrated in FIG. 12 includes a flow restrictor, a pressurizing device, and a first passive valve, connected by a fluid delivery channel. The triggerable passive valve embodiment illustrated in FIG. 12 acts upon a sample liquid, and includes a flexible bladder in the pressurizing device for increasing the pressure of air in the pressurizing device.
FIG. 13 is an illustration of the triggerable passive valve of FIG. 12 after the flexible bladder has been compressed, increasing the pressure of air in the pressurizing device and causing sample liquid to flow beyond the passive valve.
Figure 14:
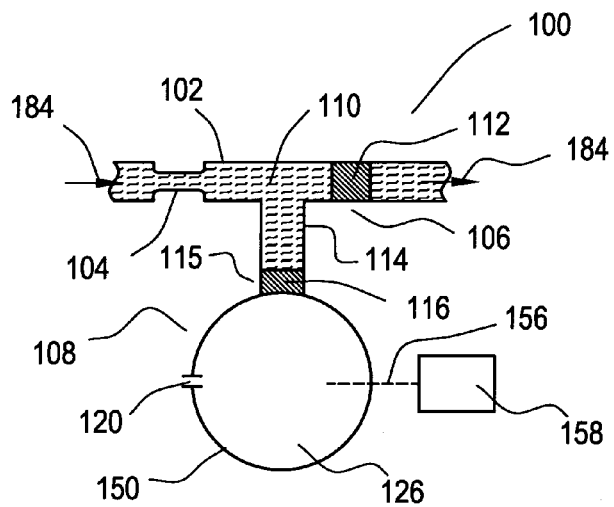
FIG. 14 is an illustration of the triggerable passive valve of FIG. 13 after the flexible bladder has been decompressed, and the air in the pressurizing device has returned to its original pressure.

Another approach can be used to initiate sample liquid flow beyond a passive valve. Instead of using heat or electrolysis to generate pressure, a flexible bladder can be used. A mechanism compresses the bladder, generating pressure and causing flow beyond a passive valve. A variety of flexible bladders can be used. In some designs a pocket is created, and at least one flexible cover is placed over the pocket. The pocket is directly connected to a flow channel and, when squeezed, it generates pressure that can be used to move sample liquid. Flexible covers can be fabricated using thin sheets of a variety of materials, such as metals and plastics. A particularly suitable material includes thin plastic films, such as 0.004" thick polyester, polycarbonate, polypropylene, polyethylene, or acrylics. Synthetic and natural rubber films can also be used. Pockets can be created using injection molding, or can be formed using die cut laminates. Mechanisms for compressing a flexible bladder can take many shapes. A particularly useful mechanism includes an electrical solenoid coupled with a plunger. When energized, the solenoid moves the plunger, making contact between the plunger and the flexible bladder. In this way, the plunger can compress the flexible bladder. Further details regarding flexible bladders, and mechanisms for compressing them, suitable for use in devices according to the present invention are included in U.S. patent application Ser. No. 10/666,846 filed on Sep. 18, 2004, and U.S. patent application Ser. No. 09/637,504 filed on Aug. 11, 2000, which are hereby incorporated by reference. FIGS. 12 through 14 are illustrations of a triggerable passive valve 100 wherein pressurizing device 108 includes a flexible bladder 150.

FIG. 12 is an illustration of another triggerable passive valve 100 according to an embodiment of the present invention. Triggerable passive valve 100 includes a flow restrictor 104, a pressurizing device 108, and a first passive valve 106, connected by fluid delivery channel 102. Triggerable passive valve 100 acts upon sample liquid 110, and includes flexible bladder 150 in pressurizing device 108 for increasing the pressure of air 126. Pressurizing device 108 also includes control channel 114, second passive valve 115, vent 120, plunger 156, and controller 158. First passive valve 106 includes hydrophobic patch 112 while second passive valve 115 includes hydrophobic patch 116. First passive valve 106 has a first burst pressure, and second passive valve 115 has a second burst pressure. The first and second burst pressures can be the same, or different. Between flow restrictor 104 and first passive valve 106 is control channel 114. Control channel 114 is connected to fluid delivery channel 102 on one end, and to second passive valve 115 on the other. Second passive valve 115 is connected to flexible bladder 150. Vent 120 allows pressure in the flexible bladder 150 to remain at atmospheric while sample liquid 110 flows through control channel 114 and to the edge of second passive valve 115. Second passive valve 115 prevents sample liquid 110 from entering flexible bladder 150. Plunger 156 can be used to increase pressure in flexible bladder 150. Plunger 156 is controlled by controller 158. Controller 158 can include an electrical solenoid, as described previously. As illustrated in FIG. 12, sample liquid 110 has entered fluid delivery channel 102 by way of the flow restrictor 104 and has stopped at both first passive valve 106 and second passive valve 115.

FIG. 13 is an illustration of the triggerable passive valve 100 of FIG. 12 after flexible bladder 150 has been compressed, increasing the pressure of air 126 and causing sample liquid 110 to flow beyond the passive valve 106. Controller 158 moves plunger 156, compressing flexible bladder 150. When plunger 156 compresses flexible bladder 150, vent 120 may be opened or closed, depending upon its design. When plunger 156 compresses flexible bladder 150 the air 126 in flexible bladder 150 in increased in pressure. As the pressure in flexible bladder 150 increases, the pressure of sample liquid 110 increases. When the pressure of sample liquid 110 exceeds the first burst pressure, sample liquid 110 flows out of control channel 114, and towards first passive valve 106 and flow restrictor 104. Arrows 180 and 182 indicate the direction in which sample liquid 110 flows. As in the designs described previously, there is less resistance to flow in the direction of arrow 182 than in the direction of arrow 180. This is due to the geometry of flow restrictor 104. Flow restrictor 104 has a higher resistance to flow than fluid delivery channel 102 in the vicinity of first passive valve 106 because the cross sectional area of flow restrictor 104 is less than that of fluid delivery channel 102. Because of the higher resistance to flow encountered at flow restrictor 104, most of the sample liquid 110 that is displaced from control channel 114 flows in the direction indicated by arrow 182. Once flow across first passive valve 106 has been established, plunger 156 decompresses flexible bladder 150, resulting in the flow that is illustrated in FIG. 14.

FIG. 14 is an illustration of the triggerable passive valve 100 of FIG. 13 after flexible bladder 150 has been decompressed, and air 126 in flexible bladder 150 has returned to atmospheric pressure. When flexible bladder 150 is decompressed, vent 120 is opened (if it is not already open), and the air 126 inflexible bladder 150 returns to atmospheric pressure. This causes sample liquid 110 in control channel 114 to flow back to second passive valve 115. Sample liquid 110 stops at second passive valve 115 because its pressure is less than the second burst pressure. Since flow over first passive valve 106 has been established, sample liquid 110 continues to flow through fluid delivery channel 102 as indicated by arrows 184 in FIG. 14.

Figure 15:
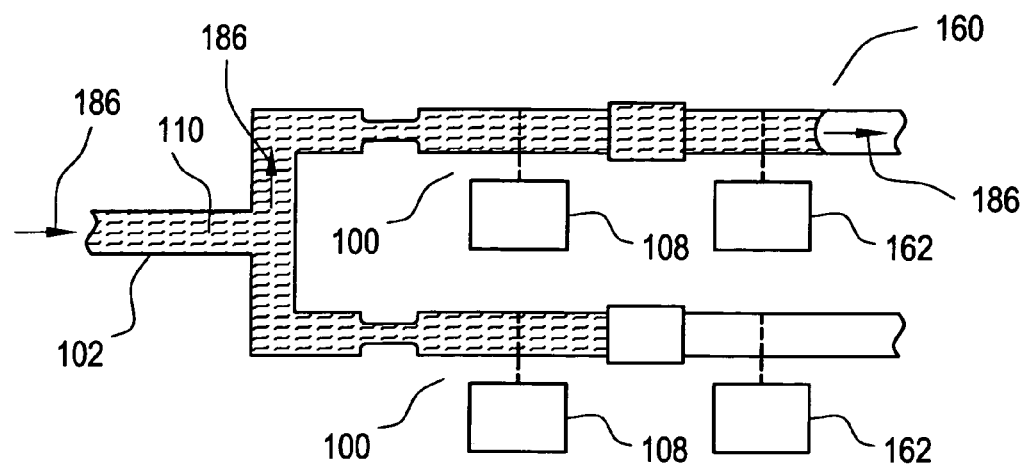
FIG. 15 is an illustration of a microfluidic circuit according to an embodiment of the present invention, wherein said microfluidic circuit includes an array of triggerable passive valves and analyte sensors arranged in parallel.

FIG. 15 is an illustration of a microfluidic circuit 160 according to an embodiment of the present invention, wherein microfluidic circuit 160 includes an array of triggerable passive valves 100 and analyte sensors 162 arranged in parallel. Microfluidic circuit 160 includes fluid delivery channel 102, triggerable passive valves 100, and analyte sensors 162. Triggerable passive valves 100 act upon sample liquid 110. Triggerable passive valves 100 can be activated sequentially or simultaneously to cause sample liquid 110 to flow over analyte sensor 162. In FIG. 15, one triggerable passive valve 100 has been activated, causing sample liquid 110 to flow over analyte sensor 162 in the direction illustrated by arrows 186.

The microfluidic circuit 160 illustrated in FIG. 15 can be used to provide a plurality of analyte sensors 162, arranged in parallel. By placing sensors 162 downstream of triggerable passive valves 100, one can measure analyte concentration in sample liquid 110. After initiating flow beyond triggerable passive valve 100, analyte concentration in sample liquid 110 can be measured for a period of time. Then, flow can be initiated beyond additional triggerable passive valve 100, and analyte concentration in sample liquid 110 measured using analyte sensor 162. In this way, one can provide an array of analyte sensors 162 arranged in parallel that can be used sequentially or simultaneously.

In a preferred embodiment, analyte sensors 162 measure glucose using electrochemistry, and sample liquid 110 is interstitial fluid, plasma, or blood. When measuring glucose, analyte sensors 162 can contain a redox reagent system that includes an enzyme and redox active compounds or mediators. A variety of mediators are known in the art, such as ferricyanide, phenazine ethosulphate, phenazine methosulfate, pheylenediamine, 1-methoxy-phenazine methosulfate, 2,6-dimethyl-1,4 benzoquinone, 2,5-dichloro-1,4-benzoquinone, ferrocene derivatives, osmium bipyridyl complexes, and ruthenium complexes. Suitable enzymes include glucose oxidase and dehydrogenase (both NAD and PQQ based). Other substances that may be present in a redox reagent system include buffering agents (e.g., citraconate, citrate, malic, maleic, and phosphate buffers); divalent cations (e.g., calcium chloride, and magnesium chloride); surfactants (e.g., Triton, Macol, Tetronic, Silwet, Zonyl, and Pluronic); and stabilizing agents (e.g., albumin, sucrose, trehalose, mannitol and lactose).

Figure 16:
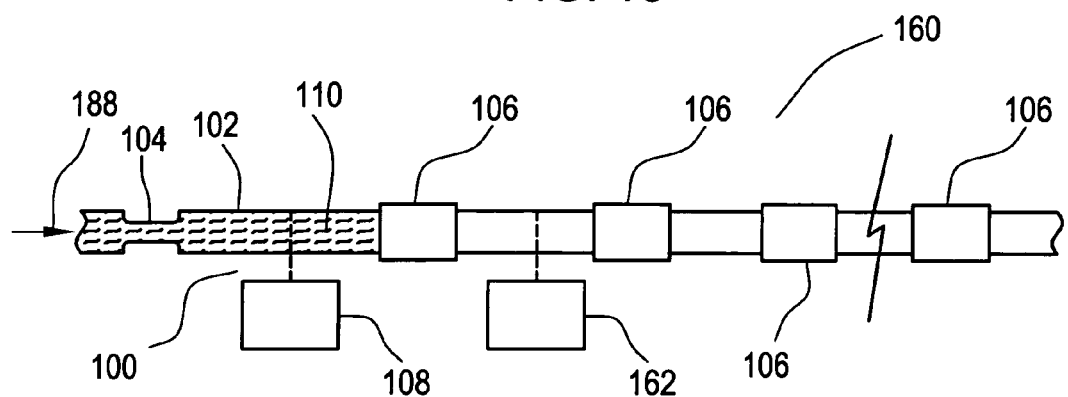
FIG. 16 is an illustration of a microfluidic circuit according to an embodiment of the present invention, wherein said microfluidic circuit includes a flow restrictor, a pressurizing device, an analyte sensor, and a serial array of passive valves.
Figure 17:
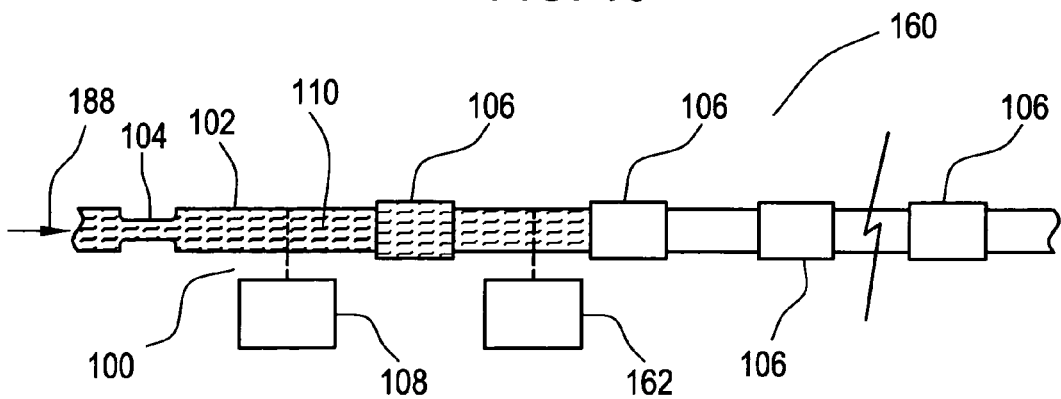
FIG. 17 is an illustration that shows flow of sample liquid through the microfluidic circuit embodiment illustrated in FIG. 16 after its pressurizing device has increased pressure on the first passive valve in series.
Figure 18:
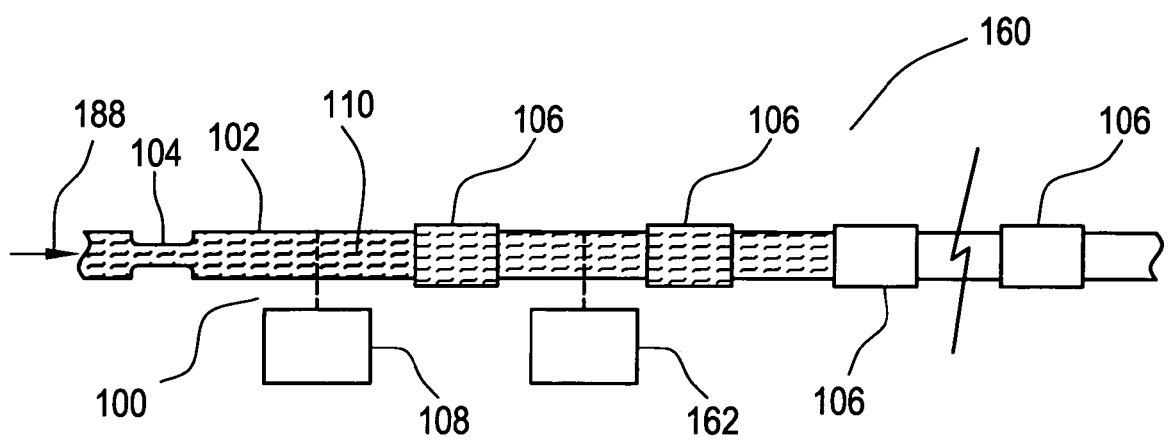
FIG. 18 is an illustration that shows flow of sample liquid through the microfluidic circuit embodiment illustrated in FIG. 16 after its pressurizing device has increased pressure on the second passive valve in series.

FIG. 16 is an illustration of a microfluidic circuit 160 according to an embodiment of the present invention, wherein microfluidic circuit 160 includes flow restrictor 104, fluid delivery channel 102, pressurizing device 108, analyte sensor 162, and a serial array of passive valves 106. Pressurizing device 108 acts upon sample liquid 110. As illustrated in FIG. 16, sample liquid 110 flows through fluid delivery channel 102 and stops at first passive valve 106. Then, pressurizing device 108 increases the pressure of sample liquid 110 to a value greater than the burst pressure of first passive valve 106. This causes sample liquid 110 to flow beyond first passive valve 106, over analyte sensor 162, and to the edge of the next passive valve 106. This is illustrated in FIG. 17. FIG. 17 is an illustration that shows flow of sample liquid 110 through microfluidic circuit 160 after pressurizing device 108 has increased pressure on the first passive valve 106 in series. Flow towards flow restrictor 104 is minimized due to its resistance. Further use of pressurizing device 108 causes sample liquid 110 to flow from one passive valve to the next, in sequence. This is illustrated in FIG. 18. FIG. 18 is an illustration that shows flow of sample liquid 110 through microfluidic circuit 160 after pressurizing device 108 has increased pressure on the second passive valve 106 in series. In this way, flow of sample liquid 110 in fluid delivery channel 102 can be stopped and then started, multiple times. In a preferred embodiment, analyte sensor 162 is in direct contact with sample liquid 110 after the first passive valve 106 is breached. Subsequently, as sample liquid 110 flows from one passive valve 106 to the next, fresh portions of sample liquid 110 contact analyte sensor 162. An advantage of this approach is that analyte sensor 162 can make measurements on stationary sample liquid 110.

Referring to FIGS. 16 through 18, measurements by analyte sensor 162 are sometimes sensitive to flow. In the case of electrochemical glucose measurement, measurements can be sensitive to flow. In most electrochemically based glucose sensors, glucose is a limiting reactant species. In the case where a glucose measurement is being attempted on sample liquid 110 while sample liquid 110 is flowing, glucose is present in excess, and is not a limiting reactant species. This causes difficulty when correlating current to glucose concentration in the liquid. For this reason, it is desirable for measurements to be made when sample liquid 110 has stopped flowing. As mentioned previously, the plurality of passive valves illustrated in FIGS. 16–18 allow sample liquid 110 to make contact with analyte sensor 162 while stationary. In a preferred embodiment of the present invention, passive valves 106 include hydrophobic patches to stop flow. As described earlier, hydrophobic patches are printed onto at least one side of the flow channel. In other embodiments of the present invention, passive valves 106 include hydrophobic patches and geometric features to stop flow. Geometric features can include sharp transitions in cross sectional area of the flow path. In the sharp transition, the cross sectional area of the flow path increases. The sharp transition creates a capillary stop, where flow stops due to surface tension at the transition in cross sectional area. In some embodiments, a hydrophobic patch may overlay a geometric feature, to enhance its ability to stop flow. Flow is stopped for at least the time necessary for analyte sensor 162 to make a measurement on sample liquid 110. Further details regarding passive valves 160 that include geometric features and/or hydrophobic patches suitable for use in devices according to the present invention are included in U.S. patent application Ser. No. 10/883,585 filed on Jun. 30, 2004, which is hereby incorporated by reference.

The microfluidic circuits 160 illustrated in FIGS. 15 through 18 can employ a variety of pressurizing devices 108, including those illustrated in FIGS. 3 through 14. The burst pressures of passive valves 106, arranged in parallel or in series, can be identical, or they can be progressively higher. In cases where they are identical, pressurizing devices 106 can be turned on and off quickly, allowing time to breach a first passive valve 106, but not a second. In the case where burst pressures of passive valves 106 are progressively higher, pressurizing devices 108 can be programmed to deliver gradually increasing pressure, in that way breaching the passive valves sequentially.

As illustrated in FIGS. 1 through 18, a number of triggerable passive valves 100 and microfluidic circuits 160 have been described. Methods of using triggerable passive valves 100 and microfluidic circuits 160 are discussed below.

Referring to FIGS. 1 and 2, a method of using triggerable passive valve 100 includes application of sample liquid 110 to fluid delivery channel 102. A next step in the method includes activation of pressurizing device 108, increasing the pressure of sample liquid 110 to a level greater than the burst pressure of first passive valve 106. In this way flow is initiated beyond first passive valve 106.

Referring to FIGS. 3 through 5, a method of using triggerable passive valve 100 starts with application of sample liquid 110 to fluid delivery channel 102. Next, sample liquid 110 flows through fluid delivery channel 102 and stops at first passive valve 106 and second passive valve 115. Electrical heater 122 is then turned on, increasing the pressure of sample liquid 110, causing it to flow beyond first passive valve 106. Electrical heater 122 is then turned off, and the pressure in air chamber 118 returns to atmospheric.

Referring to FIGS. 6 through 8, a method of using triggerable passive valve 100 is similar to that used for triggerable passive valve 100 illustrated in FIGS. 3 through 5, with the exception that sample liquid 110 makes direct contact with electrical heater 122 where a portion of sample liquid 110 is vaporized.

Referring to FIGS. 9 through 11, a method of using triggerable passive valve 100 is similar to that used for triggerable passive valve 100 illustrated in FIGS. 3 through 5, with the exception that sample liquid 110 makes direct contact with first electrode 142 and second electrode 144 where a portion of sample liquid 110 is electrolyzed.

Referring to FIGS. 12 through 14, a method of using triggerable passive valve 100 is similar to that used for triggerable passive valve 100 illustrated in FIGS. 3 through 5, with the exception that sample liquid 110 is pressurized by compressing flexible bladder 150 with plunger 156.

Referring to FIG. 15, a method of using microfluidic circuit 160 starts with application of sample liquid 110 to fluid delivery channel 102. Next, sample liquid 110 flows through fluid delivery channel 102 and stops at triggerable passive valves 100. Pressurizing device 108 is then turned on, increasing the pressure of sample liquid 110, causing it to flow beyond triggerable passive valve 100 and into contact with analyte sensor 162 where measurements on sample liquid 110 can be made. Flow can then be initiated across remaining triggerable passive valves 100 and measurements made using analyte sensors 162 either simultaneously or sequentially.

Referring to FIGS. 16, 17, and 18, a method of using microfluidic circuit 160 starts with application of sample liquid 110 to fluid delivery channel 102. After sample liquid 110 has reached passive valve 106, pressuring device 108 increases the pressure of sample liquid 110 beyond the burst pressure of passive valves 106. Sample liquid 110 then flows beyond passive valve 106, stopping at the next passive valve 106 in series, and can be analyzed using analyte sensor 162. The pressure of sample liquid 110 can then be increased again, causing sample liquid 110 to flow over the next passive valve. Sample liquid 110 can then be analyzed using analyte sensor 162. This method can be repeated as needed, for sequential measurements using analyte sensor 162.

It will be recognized that equivalent structures may be substituted for the structures illustrated and described herein and that the described embodiment of the invention is not the only structure which may be employed to implement the claimed invention. In addition, it should be understood that every structure described above has a function and such structure can be referred to as a means for performing that function. While preferred embodiments of the present invention have been shown and described herein, it will be obvious to those skilled in the art that such embodiments are provided by way of example only. Numerous variations, changes, and substitutions will now occur to hose skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A triggerable passive valve for use in controlling the flow of fluid, said triggerable passive valve comprising:
    a fluid delivery channel having an inlet for receiving fluid and an outlet for discharging fluid, said outlet being downstream from said inlet;
    a flow restrictor positioned between said inlet and said outlet;
    a first passive valve positioned in said fluid delivery channel downstream from said flow restrictor, said first passive valve having a first predetermined burst pressure, said first passive valve preventing fluid from moving through said channel when the pressure exerted by said fluid on said first passive valve is below said burst pressure;

a control channel having an inlet and an outlet, said control channel outlet being connected to said fluid delivery channel between said flow restrictor and said first passive valve;

a pneumatic actuator connected to said control channel at said control channel inlet; and a second passive valve positioned in said control channel between said control channel inlet and said control channel outlet.

2. A triggerable passive valve for use in controlling the flow of fluid comprising:

a fluid delivery channel having an inlet for receiving fluid and an outlet for discharging fluid downstream from said inlet;

a flow restrictor positioned between said inlet and said outlet, said flow restrictor comprising:

a length of said delivery channel having a cross sectional area which is smaller than a cross sectional area of said channel at said inlet;

a first passive valve positioned in said fluid delivery channel downstream from said flow restrictor, said first passive valve having a first predetermined burst pressure, said first passive valve preventing fluid from moving through said fluid delivery channel when the pressure exerted by said fluid on said first passive valve is below said burst pressure, said first passive valve comprising:

a hydrophobic patch positioned on one wall of said fluid delivery channel, said hydrophobic patch comprising:

a material having a contact angle of between seventy and one hundred eighty degrees;

a control channel having an inlet and an outlet, said control channel outlet being connected to said fluid delivery channel between said flow restrictor and said first passive valve;

a pneumatic actuator connected to said control channel at said control channel inlet, said pneumatic actuator comprising:

an air chamber;

an electrical heater adapted to heat air in said air chamber;

a controller connected to said electrical heater;

a vent, positioned to release air from said pneumatic actuator when pressure in said pneumatic actuator exceeds a predetermined limit; and a second passive valve positioned in said control channel between said control channel inlet and said control channel outlet, said second passive valve comprising:

a hydrophobic patch positioned on one wall of said fluid delivery channel, said hydrophobic patch comprising:

a material having a contact angle of between seventy and one hundred eighty degrees.

3. A triggerable passive valve for use in controlling the flow of fluid comprising:

a fluid delivery channel having an inlet for receiving fluid and an outlet for discharging fluid downstream from said inlet;

a flow restrictor positioned between said inlet and said outlet;

a first passive valve positioned in said fluid delivery channel downstream from said flow restrictor, said first passive valve having a first predetermined burst pressure, said first passive valve preventing fluid from moving through said channel when the pressure exerted by said fluid on said first passive valve is below said burst pressure;

a bubble chamber connected to said fluid delivery channel between said flow restrictor and said first passive valve.

4. A triggerable passive valve for use in controlling the flow of fluid comprising:

a fluid delivery channel having an inlet for receiving fluid and an outlet for discharging fluid downstream from said inlet;

a flow restrictor positioned between said inlet and said outlet, said flow restrictor comprising:

a length of said delivery channel having a cross sectional area which is smaller than a cross sectional area of said channel at said inlet;

a first passive valve positioned in said fluid delivery channel downstream from said flow restrictor, said first passive valve having a first predetermined burst pressure, said first passive valve preventing fluid from moving through said channel when the pressure exerted by said fluid on said first passive valve is below said burst pressure, said first passive valve comprising:

a hydrophobic patch positioned on one wall of said fluid delivery channel, said hydrophobic patch comprising:

a material having a contact angle of between seventy and one hundred eighty degrees;

a control channel having an inlet and an outlet, said control channel outlet being connected to said fluid delivery channel between said flow restrictor and said first passive valve;

a bubble chamber connected to said fluid delivery channel between said flow restrictor and said first passive valve, said bubble chamber comprising:

an electrical heater adapted to heat fluid in said fluid delivery channel, wherein said electrical heater comprises a resistor;

a controller connected to said electrical heater; and a second passive valve positioned in said control channel between said control channel inlet and said control channel outlet, said second passive valve comprising:

a hydrophobic patch positioned on one wall of said fluid delivery channel, said hydrophobic patch comprising:

a material having a contact angle of between seventy and one hundred eighty degrees.

5. A triggerable passive valve for use in controlling the flow of fluid comprising:

a fluid delivery channel having an inlet for receiving fluid and an outlet for discharging fluid downstream from said inlet;

a flow restrictor positioned between said inlet and said outlet, said flow restrictor comprising:

a length of said delivery channel having a cross sectional area which is smaller than a cross sectional area of said channel at said inlet;

a first passive valve positioned in said fluid delivery channel downstream from said flow restrictor, said first passive valve having a first predetermined burst pressure, said first passive valve preventing fluid from moving through said channel when the pressure exerted by said fluid on said first passive valve is below said burst pressure, said first passive valve comprising:

a hydrophobic patch positioned on one wall of said fluid delivery channel, said hydrophobic patch comprising:

a material having a contact angle of between seventy and one hundred eighty degrees;
a control channel having an inlet and an outlet, said control channel outlet being connected to said fluid delivery channel between said flow restrictor and said first passive valve;
a bubble chamber connected to said fluid delivery channel between said flow restrictor and said first passive valve, said bubble chamber comprising:
an electrical heater adapted to heat fluid in said fluid delivery channel, wherein said electrical heater comprises a pair of opposed electrodes;
a controller connected to said electrical heater; and
a second passive valve positioned in said control channel between said control channel inlet and said control channel outlet, said second passive valve comprising:
a hydrophobic patch positioned on one wall of said fluid delivery channel, said hydrophobic patch comprising:
a material having a contact angle of between seventy and one hundred eighty degrees.

* * * * *